United States Patent [19]

Ueno et al.

[11] Patent Number: 5,475,026
[45] Date of Patent: Dec. 12, 1995

[54] AGENT FOR TREATING HEPATIC DISEASES

[75] Inventors: Shinya Ueno, Kamakura; Shintaro Nishio, Ebina, both of Japan

[73] Assignee: Toray Industries, Inc., Tokyo, Japan

[21] Appl. No.: 78,298

[22] PCT Filed: Oct. 23, 1992

[86] PCT No.: PCT/JP92/01382

§ 371 Date: Jun. 25, 1993

§ 102(e) Date: Jun. 25, 1993

[87] PCT Pub. No.: WO93/07876

PCT Pub. Date: Apr. 29, 1993

[30] Foreign Application Priority Data

Oct. 25, 1991 [JP] Japan ................................. 3-279840

[51] Int. Cl.$^6$ ..................................................... A61K 31/34
[52] U.S. Cl. .................................................... 514/468
[58] Field of Search ........................................ 514/468

[56] References Cited

U.S. PATENT DOCUMENTS 4,474,802 10/1984 Ohno et al. ............................... 424/285

FOREIGN PATENT DOCUMENTS 2088856  6/1982  United Kingdom .
86/00808  2/1986  WIPO .

OTHER PUBLICATIONS

Murata et al., Arzneim.–Forsh./Drug Research 39 (II), Nr. 8 (1989) pp. 867–876.
Chemical Abstracts 114:163859.

Database Biosis, Biosciences Information Service, AN:90:158620 1989, Nishio, S. et al., vol. 94, No. 6, pp. 351–362.

Database WPI, Week 8733, Derwent Pub. Ltd., AN 87–229612 & EP–A–0 232 776 (abstract) 1987.

Official Journal Of The American Association For The Study Of Liver Diseases, vol. 16, No. 4PT2, Oct. 1992, p. 161A.

*American Physiological Society*, H. Araki et al., 1980, pp. H176–H181: "Cytoprotective Actions Of Prostacyclin . . . Cat Liver".

*Experimental and Molecular Pathology* 42, 163–166 (1985), A. Divald et al., "Hepatoprotective Effects of Prostacyclins . . . in Rats".

*Hepatology*, vol. 7, No. 6, pp. 1184–1188, 1987, Y. Mizoguchi et al., "The Protective Effects of Prostaglandin . . . Necrosis Model".

*Gastroenterology* 1981; 81:211–217, J. Stachura et al., "Protaglandin Protection of Carbon Tetrachloride–Induced Liver Cell Necrosis . . . ".

*Klin Wochenschr* (1986) 64 (Suppl. VII): 47–50, W. Bursch et al., "Cytoprotective Effect of the Prostacyclin . . . and Bromobenzene".

Fujiwara et al., AASLD Abstract. Hepatology 16 (4 Part 2), 1992.

*Primary Examiner*—Raymond Henley, III
*Assistant Examiner*—Phyllis G. Spivack
*Attorney, Agent, or Firm*—Birch, Stewart, Kolasch & Birch

[57] ABSTRACT

Beraprost, a agent for treating hepatic diseases, that is safe and chemically stable is disclosed.

6 Claims, No Drawings

AGENT FOR TREATING HEPATIC DISEASES

This application is a 371 of PCT/JP92/0/382, filed Oct. 23, 1992.

TECHNICAL FIELD

This invention relates to an agent for treating hepatic diseases.

BACKGROUND ART

It is well-known that the liver is an important organ which controls the metabolism of the body. It is said that as many as 40,000 people die of hepatic diseases in Japan in a year. Hepatic diseases such as hepatonecrosis, fatty liver, disorders of bile secretion, and cirrhosis are caused by the fact that the liver is acutely or chronically diseased by various factors such as alcohol, lack of nutrients, infection by viruses, chemical toxins and the like. At present, no drug which exhibits a prominent pharmacological effect for the treatment and prophylaxis of these hepatic diseases when orally administered has been discovered.

DISCLOSURE OF THE INVENTION

The object of the present invention is to provide an agent for treating hepatic diseases, which has excellent effect for curing hepatic diseases, which is stable, which can be administered not only parenterally, but also orally and which is safe.

The present inventors made extensive studies for developing an agent for treating hepatic diseases having excellent effectiveness and practicality to discover that beraprost is stable and has a prominent effect for promoting the functions of the liver, thereby completing the present invention.

That is, the present invention provides an agent for treating hepatic diseases comprising as an effective ingredient beraprost or a pharmaceutically acceptable salt thereof.

The agent for treating hepatic diseases according to the present invention has excellent effect in curing various hepatic diseases and is safe. Further, it is chemically stable, so that it can be orally administered.

BEST MODE FOR CARRYING OUT THE INVENTION

The compound (±)-(1R*,2R*, 3aS*,8bS*)-2,3,3a,8b-tetrahydro-2-hydroxy-1-[(E)-(3S*)-3-hydroxy-4methyl-1-ocetene-6-inyl]-1H-cyclopenta[b]benzofuran-5-butyric acid (beraprost is used as an agent for inhibiting tumor metastasis. This compound has the following structure.

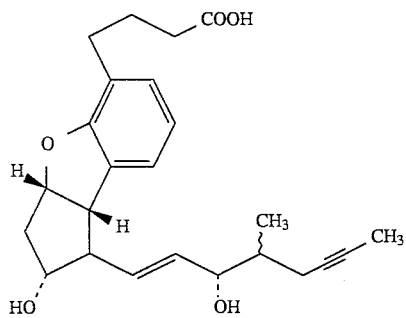

Beraprost is described in Japanese Laid-open Patent Application (Kokai) Nos. 58-32277, 57-144276 and 58-124778 and the like as a $PGI_2$ derivative having a skeleton in which the exoenol moiety characteristic to beraprost is converted to an inter-m-phenylene structure. However, it is not known that beraprost has activity to cure hepatic diseases.

The beraprost which is an effective ingredient of compositions of the present invention includes not only the racemic form, but also d-form and l-form. Beraprost can be produced by, for example, the method described in the abovementioned Japanese Laid-open Patent Application (Kokai) No. 58-124778. The salts of beraprost include any pharmaceutically acceptable salts including alkaline metal salts such as sodium salt and potassium salt; alkaline earth metal salts such as magnesium salt and calcium salt; ammonium salt; primary, secondary and tertiary amine salts; and basic amino acid salts.

When orally or parenterally administered, beraprost exhibits prominent effect in promoting the functions of the liver. Alternatively, a reduction in decrease of liver function due to disease is observed upon administration of berapost. More particularly, the agent for treating hepatic diseases according to the present invention is effective for treating acute and chronic hepatic diseases such as fatty liver, alcoholic hepatitis, toxic hepatic disorders, congestive liver, disorders of bile secretion, stagnation hepatic disorders, ischemic hepatic disorders, hepatic insufficiency, fulminating hepatitis and cirrhosis. Further, the agent is also effective for promoting functions of the liver suffering from hepatic disorders after surgery, and in ameliorating the decline in liver function due to viral hepatic disease and liver cancer. The agent is also effective for the protection of the liver during transplantation and for promoting the functions of the liver after transplantation.

The dose of administration of the compound differs depending on the type and degree of the disease to be treated. In cases where acute or chronic hepatic diseases such as fatty liver, alcoholic hepatitis, toxic hepatic disorders, disorders of bile secretion, and cirrhosis, beraprost is administered in a dose of 0.01–100 mg/g and 1–3 times a day.

Although beraprost or a salt thereof alone may be administered, the agent for treating hepatic diseases according to the present invention may also be administered in the form of a solid containing the additives described below.

Examples of the additives include vehicles such as starches, lactose, sucrose, glucose, mannitol, calcium carbonate, calcium sulfateand the like; binding agents such as starches, dextrin, gum arbicae, tragacanth, methyl cellulose, gelatin, polyvinylpyrrolidone, polyvinyl alcohol or the like; a disintegrator such as starches, polyvinylpyrrolidone, crystalline cellulose and the like; lubricants such as magnesium stearate, talc and the like; coloring agents; and perfumes.

The formulation may be in the form of tablets, sugar-coated tablets, powder, granules, troches, capsules, balls and syrups.

For parenteral administration, the composition may be formulated into an aqueous sterilized solution. The solution may contain other solutes such as sodium chloride or glucose in an amount sufficient to make the solution isotonic.

Since the agent for treating hepatic diseases according to the present invention has a stable chemical structure, there is no difficulty in formulating the compound. Thus, in addition to the above-described formulations for oral administration, the compound may easily be formulated in the form of various solutions for injection and suppositories.

EXAMPLE

The invention will now be described in more concretely by way of examples thereof. However, the present invention is not restricted to the examples.

EXAMPLE 1

Using 7 week-old Sprague-Dawley (hereinafter referred to as "SD") male rats, the effectiveness of beraprost against hepatic disorder induced by carbon tetrachloride was tested employing two administration routes, that is, oral and intraperitoneal administrations. Each group consisted of 6 rats. The test compound was the sodium salt of beraprost. The test compound was administered to the rats. which had been fasted for 24 hours, One hour after beraprost administration, 12.5% carbon tetrachloride solution in olive oil was administered in a dose of 2 ml/kg. The carbon tetrachloride solution was intraperitoneally administered to the rats to which the test compound was orally administered. The carbon tetrachloride solution was orally administered to the rats to which the test compound was intraperitoneally administered. After the administration of the carbon tetrachloride solution, the rats were fasted for 24 hours, and the glutamic acid-oxalic acid transaminase (hereinafter referred to as "GOT") level in serum was measured. As a control group, one group was treated in the same manner as described above except that the sodium salt of beraprost was not administered. The results are shown in

TABLE 1

| Administration Route | Dose (mg/kg) | GOT (unit/l) |
|---|---|---|
| Oral | Control | 15647 ± 1588 |
|  | 0.3 | 3820 ± 642 |
| Intraperitoneal | Control | 11943 ± 1216 |
|  | 0.3 | 1889 ± 506 |

As shown in Table 1, in the groups to which sodium salt of beraprost was administered, significant decrease in GOT was observed. Thus, it was confirmed that hepatic disorder was improved by administration of beraprost.

EXAMPLE 2

Using 7 week-old SD male rats, the effectiveness of beraprost by oral administration against the hepatic disorder induced by D-galactosamine was tested. As the test compound, the sodium salt of beraprost was used. The test compound was administered in a dose of 0.3 mg/kg per each time at one hour before and 6 hours after the administration of D-galactosamine. D-galactosamine was subcutaneously administered in a dose of 1 g/kg. Forty eight hours after the administration of D-galactosamine, the GOT and glutamic acid-pyruvic acid transaminase (hereinafter referred to as "GPT") levels in serum, and the content of triglyceride in the livers were measured.

As a control group, one group was treated in the same manner as described above except that sodium salt of beraprost was not administered. As a non-treated group, one group did not receive D-galactosamine. The results are shown in Table 2.

TABLE 2

| Group | GOT (unit/l) | GPT (unit/l) | Triglyceride (mg/g tissue) |
|---|---|---|---|
| Non-treated Group | 154 ± 7 | 79 ± 5 | 14.1 ± 0.6 |
| Control Group | 5641 ± 858 | 2552 ± 375 | 42.4 ± 6.0 |
| Test Group | 3506 ± 377 | 1356 ± 187 | 12.4 ± 0.7 |

As shown in Table 2, significant decreases in serum GOT, GPT and the amount of triglycerides in the liver were observed in the test group (the group to which the test compound was administered) when compared with the control group. Thus, it was confirmed that beraprost has an activity to improve hepatic disorders.

EXAMPLE 3

Using 7 week-old SD male rats, each group consisting of 6 rats, the effectiveness of beraprost by oral administration against the increase in the lipid peroxide level in the blood induced by carbon tetrachloride was tested. The sodium salt of beraprost was used as the test compound. 12.5% carbon tetrachloride solution in olive oil was intraperitoneally administered in a dose of 2 ml/kg to the rats which had been fasted for 24 hours. After the administration of the carbon tetrachloride solution, the rats were fasted for another 24 hours and then the levels of lipid peroxide, GOT and GPT in serum were measured. The test compound was administered one hour before (Test Group 1) or 6 hours after (Test Group 2) the administration of the carbon tetrachloride solution. As a control group, one group was treated in the same manner as described above except that the sodium salt of beraprost was not administered. As a non-treated group, one group did not receive carbon tetrachloride. The results are shown in Table 3.

TABLE 3

| Group | GOT (unit/l) | GPT (unit/l) | Lipid Peroxides (mmol/ml) |
|---|---|---|---|
| Non-treated Group | 95 ± 5 | 21 ± 2 | 3.40 ± 0.21 |
| Control Group | 14689 ± 1577 | 3709 ± 406 | 7.10 ± 1.73 |
| Test Group 1 | 4428 ± 1649 | 1285 ± 344 | 2.44 ± 0.34 |
| Test Group 2 | 7672 ± 1834 | 1713 ± 258 | 2.82 ± 0.52 |

As shown in Table 3, by the administration of the test compound one hour before or 6 hours after the administration of the disorder-causing substance, a significant decrease in GOT, GPT and lipid peroxide level in the blood was observed. Thus, it was confirmed that beraprost has an activity to improve hepatic disorders. Particularly, since a significant effect for improving hepatic disorder was observed even when the compound was orally administered 6 hours after the administration of the disorder-causing substance, it was shown that the compound has a strong effect for improving hepatic disorders.

EXAMPLE 4

Using 8–10 week-old SD male rats, the effectiveness of beraprost by oral administration against the disorder caused by liver ischemia-recirculation was tested. The sodium salt of beraprost was used as the test compound. The test compound was administered 30 minutes before the induction of liver ischemia. The doses of the administered test compound were as shown in Table 4. Liver ischemia was induced by ventrotomy under anesthesia and closing the hepatic artery in the outer left leaf and the portal vein with clips. One hour after the clipping, the clips were removed to reopen the vessels. Two hours after recirculation, the GPT level in serum was measured to evaluate the degree of disorder.

As a control group, one group was treated in the same manner as described above except that distilled water was administered in place of sodium salt of beraprost. The results are shown in Table 4.

TABLE 4

| Concentration of Test Compound (mg/kg) | GPT (unit/l) |
|---|---|
| 0 (control group) | 624 |
| 0.03 | 617 |
| 0.1 | 540 |
| 0.3 | 427 |

As shown in Table 4, by the administration of sodium salt of beraprost, a decrease in GPT level in serum was observed. Thus, it was confirmed that beraprost has an activity to improve the hepatic disorder caused by ischemia of the liver.

EXAMPLE 5

[Acute Toxicity Test]

Acute toxicity test was carried out using rats. $LD_{50}$ values of the compound for each administration route and sex are shown in Table 5.

As for the pathological symptoms, the main symptoms which were common to male and female and to all of the administration routes were, in the cases wherein the mice were killed, slight to medium congestion in lung, slight to medium bleeding in stomach glands and slight small intestine catarrh.

Thus, it was clarified that side effects are observed only at very high dose.

TABLE 5

| Administration Route | Observation Period (Days) | Sex | Number of Animals | $LD_{50}$* (mg/kg) |
|---|---|---|---|---|
| Oral | 14 | Male | 10 | 15 (13–19) |
| Oral | 14 | Female | 10 | 12 (9–15) |
| Intravenous | 14 | Male | 10 | 18 (15–22) |
| Intravenous | 14 | Female | 10 | 13 (10–16) |
| Subcutaneous | 14 | Male | 10 | 13 (12–14) |
| Subcutaneous | 14 | Female | 10 | 7 (6–9) |

*Litchfield-Wilcoxon Method (see J. Pharmacol. Expl. Therap. Vol. 96, p. 99 (1949)
The numbers in parentheses indicate 95% reliable limit.

EXAMPLE 6

Tablets according to the present invention were prepared according to the prescription shown in Table 6.

TABLE 6

| Component | | mg/tablet |
|---|---|---|
| Crude Tablets | | |
| Beraprost | | 0.02 |
| Lactose | | 64.98 |
| Corn Starch | | 25.00 |
| Crystalline Cellulose | | 7.50 |
| Hydroxypropylcellulose | | 2.20 |
| Magnesium Stearate | | 0.30 |
| | Subtotal | 100.00 |
| Film | | |
| Hydroxypropylmethylcellulose 2910 (Pharmacopedia) | | 4.70 |
| Macrogol 6000 (Pharmacopedia) | | 0.30 |
| Carnauba wax | | Small Amount |
| | Subtotal | 5.00 |
| | Total | 105.00 |

INDUSTRIAL APPLICABILITY

The agent for treating hepatic diseases according to the present invention exhibits effectiveness for the treatment and prophylaxis of various hepatic diseases. Further, it is chemically stable. Therefore, it can be used for treating and preventing hepatic disorders by systemic administration.

We claim:

1. A method for treating hepatic diseases comprising administering an amount of beraprost effective for treating hepatic disease to a patient suffering from a hepatic disease.

2. A method according to claim 1, wherein said amount of beraprost ranges from 0.01 to 100 mg per kg of patient per day.

3. A method according to claim 1, wherein said amount of beraprost ranges from 0.1 to 0.3 mg/kg.

4. A method according to claim 1, wherein the beraprost is administered prophylactically.

5. A method according to claim 2, wherein the beraprost is administered prophylactically.

6. A method according to claim 3, wherein the beraprost is administered prophylactically.

* * * * *